United States Patent [19]

Miyazawa

[11] 4,448,526
[45] May 15, 1984

[54] DEFECT DETECTING METHOD AND DEVICE

[75] Inventor: Takashi Miyazawa, Urayasu, Japan

[73] Assignee: Kirin Beer Kabushiki Kaisha, Tokyo, Japan

[21] Appl. No.: 272,792

[22] Filed: Jun. 11, 1981

[30] Foreign Application Priority Data

Jun. 27, 1980 [JP] Japan .................................. 55-87510
Jun. 27, 1980 [JP] Japan .................................. 55-87511

[51] Int. Cl.³ .......................................... G01N 21/00
[52] U.S. Cl. ................................ 356/237; 250/223 B; 250/572; 356/240
[58] Field of Search ............... 356/237, 234, 240, 428; 250/223 B, 563, 572; 209/526, 527, 582, 588; 358/106

[56] References Cited

U.S. PATENT DOCUMENTS

| | | | |
|---|---|---|---|
| 2,649,500 | 8/1953 | Fedorchak | 358/106 |
| 3,529,167 | 9/1970 | Calhoun | 250/223 B |
| 3,987,244 | 10/1976 | Messman | 358/106 |
| 4,256,957 | 3/1981 | Ford et al. | 250/223 B |

FOREIGN PATENT DOCUMENTS

2848316  5/1980  Fed. Rep. of Germany ...... 358/106

OTHER PUBLICATIONS

Mengers, "Digital Video Systems Applied to Product Inspection", *Proc. SPIE*, vol. 170, pp. 43-50 1979.

*Primary Examiner*—William L. Sikes
*Assistant Examiner*—Matthew W. Koren
*Attorney, Agent, or Firm*—Ladas & Parry

[57] ABSTRACT

In a defect detecting method and device, image formed by receiving light from an illuminated object to be examined, is divided into a plurality of picture elements, and the signals of the picture elements are stored. The signals are later read out in the order in which the portions of the object corresponding respectively to the picture elements are traversed by a substantially spiral imaginary line drawn on said object, and a defect is detected from the relationship between the signal of one of the picture elements and the signal of another picture element read out a little before the reading of the signal of said one of the picture elements.

9 Claims, 21 Drawing Figures

DIRECTION OF SCANNING

| X<br>Y | 1 | 2 | 3 | ... | 100 |
|---|---|---|---|---|---|
| 1 | 0 0 0 0 0 0 | 0 0 0 0 0 1 | 0 0 0 0 0 1 | | 0 0 0 0 0 0 |
| 2 | 0 0 0 0 0 0 | 0 0 0 0 1 0 | 0 0 0 0 1 1 | | 0 0 0 0 0 0 |
| 3 | 0 0 0 0 0 0 | 0 0 0 0 1 1 | 0 0 0 1 0 0 | | 0 0 0 0 0 1 |
| 4 | 0 0 0 0 0 0 | 0 0 0 0 1 1 | 0 0 0 1 1 0 | | 0 0 0 0 1 0 |
| ... | | | | | |
| 100 | 0 0 0 0 0 0 | 0 0 0 0 0 1 | 0 0 0 0 1 0 | | 0 0 0 0 0 0 |

50
JUDGING CIRCUIT

DEFECT DETECTING METHOD AND DEVICE

BACKGROUND OF THE INVENTION

This invention relates to a method of detecting defects in an object, for example, a bottle in which the degrees of scratches, cracks or breakage of objects to be examined such as beer bottles or juice bottles and the presence or absence of foreign matters in the objects are optically detected, and to a device for implementing the method.

In general, bottles used for beer, wine, carbonated drinks, food, etc. are recovered and used again. The bottles thus recovered are cleaned with a bottle cleaning device to remove foreign matters such as dust and leavings. However, the bottle cleaning device is unable to remove some of foreign matters stuck firmly to the inner wall of a bottle. Therefore, it is necessary to remove bottles having foreign matters from the bottling line before or after the bottle cleaning process. It is also necessary to remove bottles having cracks or scratches.

Various methods or devices for detecting bottle defect have been conceived or proposed, but they are associated with a disadvantage or another, which will be described in detail later.

SUMMARY OF THE INVENTION

Accordingly, an object of this invention is to provide a defect detecting method in which the drawbacks accompanying a conventional defect detecting method have been eliminated, and a device for implementing the method.

Another object of the invention is to provide a defect detecting method in which a video signal can be processed so that the effect of optical disturbances at the edge of the bottom of a bottle is minimized, and a device for implementing the method.

A further object of the invention is to provide a defect detecting method in which defects in the bottom of a bottle can be detected with high accuracy and the result of the detection can be processed at high rate, and a device for implementing the method.

A still further object of the invention is to provide a defect detecting device having the above-described specific features which can be manufactured at low cost.

According to one aspect of the invention, there is provided a defect detecting method comprising the steps of:

(a) illuminating an object to be examined;

(b) receiving light from the object to form the image of the object;

(c) dividing the image of said object into a plurality of picture elements;

(d) storing the signals of the picture elements in relation with the positions of portions of the objects to which the picture elements correspond respectively;

(e) reading the signals of the picture elements in the order in which the portions of the object corresponding respectively to the picture elements are traversed by a substantially spiral imaginary line which is drawn on said object; and (f) detecting a defect in the object from the mutual relationship between the signal of one of the picture elements and the signal of another picture element read out a little before the reading of the signal of said one of the picture elements.

According to another aspect of the invention, there is provided a defect detecting device comprising:

(a) a device for illuminating an object to be examined;

(b) a device for receiving light from the object, to form the image of the object;

(c) a storing device for storing signals representative of picture elements forming the image in relation to portions of the object which correspond to the picture elements, respectively;

(d) a reading device for reading the signals representative of the picture elements in the order in which the portions of the object to which the picture elements correspond respectively are traversed by a substantially spiral imaginary line which is drawn on the object; and (e) a detecting device for detecting a defect in the object from the mutual relationship between the signal of one of the picture elements and the signal of another picture element read out a little before the reading of the signal of said one of the picture elements.

The foregoing objects and other objects as well as characteristic features of the invention will become more apparent from the following detailed description and the appended claims when read in conjunction with the accompanying drawings.

DETAILED DESCRIPTION OF THE PREFERRED EMBODIMENTS

Before describing the preferred embodiments of the invention, disadvantages of the methods and systems which have been either conceived or proposed are described briefly to facilitate understanding of features and merits of the invention.

Figure 1A:
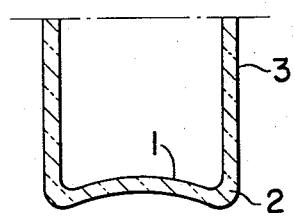
FIG. 1A is a sectional view of the bottom of a bottle.

In one method which has been conceived, an electric lamp is disposed under the bottle bottom to irradiate the bottle, while a television camera is arranged over the bottle to subject the optical image of the bottle to photo-electric conversion to provide an electrical signal, and the electrical signal is delivered out through the scanning operation of the television camera. However, the method is disadvantageous in that it is difficult to improve the accuracy in detecting defects at the edge or corner of the bottle bottom because of optical disturbance of relatively high level produced at the corner. As shown in FIG. 1A, the bottle bottom 1 is joined to the bottle barrel 3 at the corner 2, and the corner 2 has a curvature and larger in thickness. In the case of a recovered bottle, its bottom often has fine scratches (which do not necessarily inhibit reuse of the bottle). Thus, the corner 2 of the bottle is often associated with optical disturbance of relatively high level.

Furthermore, after a bottle has been cleaned, a small amount of cleaning solution may remain in the bottle. With remaining cleaning solution, scattering light beams from under the bottom are subjected to total reflection at the meniscus of the cleaning solution, and will not reach the light receiving unit provided over the bottle. The resultant optical image of the bottle bottom contains a dark ring pattern corresponding to the corner 2.

Figure 1B:
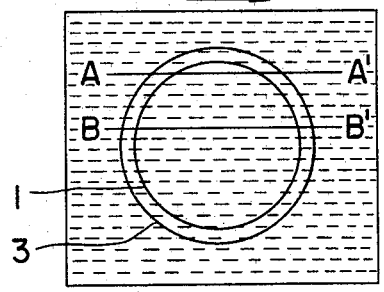
FIG. 1B is an explanatory diagram showing the relationship between the optical image of the bottle bottom and scanning lines.
Figure 1C:
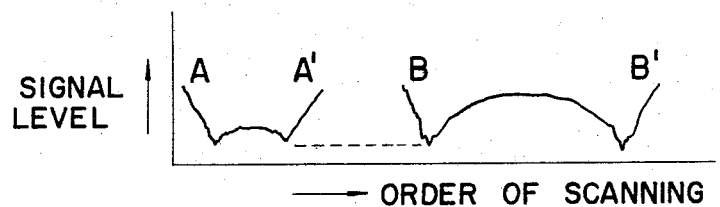
FIG. 1C is a graphical representation indicating scanning direction with signal level, with respect to parts A-A' and B-B' in FIG. 1B.

Because of a variety of optical disturbances as described above, the output electrical signal of the television camera obtained by optically scanning the bottle bottom 1 in a manner as shown in FIG. 1B, is as shown in FIG. 1C. As will be seen, the signal level for the corner 2 is lower. Especially in the part A-A', the signal level is low from the beginning to the end and the waveform is intricate, and accordingly, it is difficult to distinguish a signal representing the normal portion from a signal representing a portion with defect which causes brightness reduction.

In order to eliminate this difficulty, a method has been conceived in which electrical gate means is provided (as disclosed in the specification of Japanese Patent Application No. 123506/1978 or a mechanical mask (using a reticle for instance) is provided so that the portion corresponding to the corner 2 is set out of the scanning range, and only the portion of the bottom which is sufficiently away from the corner is subjected to inspection. This will solve the problem of reduction in accuracy due to the wear of the machine and the eccentricity of the bottle positioned for inspection, relative to the light receiving unit.

As has been described, a television camera is often employed as an image pickup means in a device for detecting defects in a glass bottle or the like. However as has been also described, it is difficult to identify a signal representative of a defect at the corner of a bottle by resorting directly to a video signal transmitted in the television scanning system, because the video signal is affected by the optical disturbance caused at the corner of the bottom of the bottle. According to this invention, such a video signal is read after being rearranged according to the configuration of an object to be examined, so that a normal signal and a signal representative of a defect (hereinafter referred to as "a defect signal", when applicable) can be distinguished, without failure, from each other.

Figure 2:
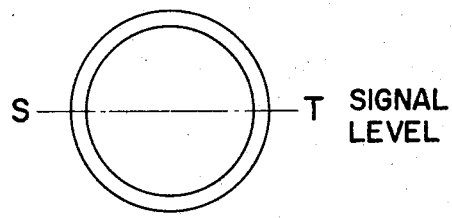
FIG. 2 is an explanatory diagram showing one example of the optical image of a bottle bottom.
Figure 3:
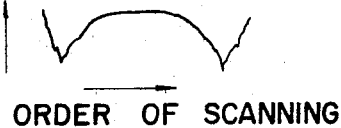
FIG. 3 is a diagram showing a signal level taken along a line S-T in FIG. 2.
Figure 4A:
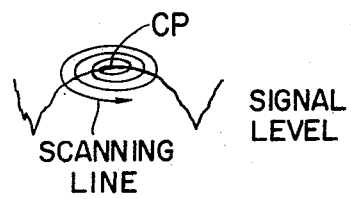
FIGS. 4A and 4B are diagrams for a description of the principle of this invention.
Figure 4B:
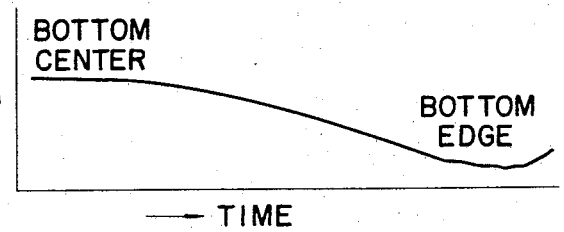

The optical image of a bottle bottom is as shown in FIG. 2, and the signal level for a line S-T is as shown in FIG. 3. This signal is stored in a memory, and then the signal thus stored is read out by a spiral scanning process in which scanning is effected spirally beginning, for example, with the center CP of the bottle bottom, as shown in FIG. 4A. The resultant signal is such that its level is gradually varied or "continuous" as long as there is no defect, from the center of the bottom to the corner or edge of the bottom, as shown in FIG. 4B. If there is a defect, there will be a sudden change in the level of the signal, so that the defect can be readily detected.

Figure 5:
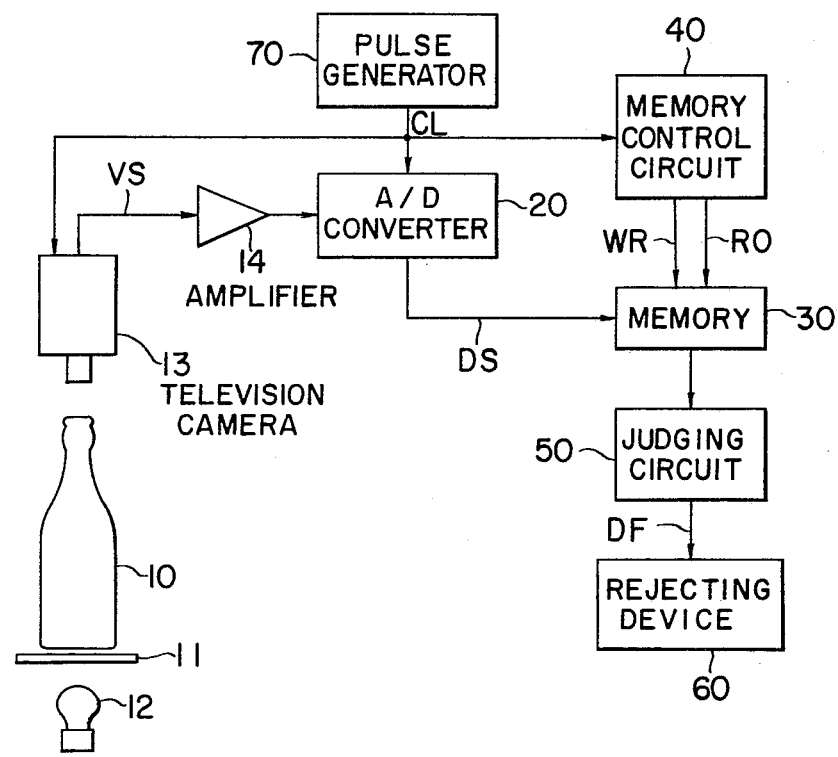
FIG. 5 is a block diagram showing one embodiment of the invention.

In one embodiment of this invention, as shown in FIG. 5, a light source, or a lamp 12, is disposed under the bottom of a bottle 10 (which is an object such as a beer bottle to be examined) and a diffusing plate 11 is interposed between the lamp 12 and the bottom. A television camera 13 is arranged over the bottle 10. The output video signal VS of the television camera 13 is amplified by an amplifier 14, and is sampled and converted into a digital signal DS (having eight or six bits for instance) by an A/D (analog-to-digital) converter 20, which is a signal representative of the brightness of a portion of the bottle to which a picture element corresponds. The digital signals DS are successively stored, as data for the picture elements respectively corresponding to the portions of the bottle, in addresses specified in a memory 30. The data stored in the memory 30 is read out in response to a read signal RO provided by a memory control circuit 40. The presence or absence of a defect warranting rejection of the bottle is judged by a judging circuit 50 according to the variation of the data thus read out.

When it is determined that the bottle has a defect, because of which the bottle should be rejected, the judging circuit 50 outputs a defect signal DF, and a bottle rejecting device 60 rejects or discharges the defective bottle through the conveyor line. A pulse generator 70 is provided to synchronize the scanning operation of the television camera 13, the analog-to-digital conversion of the A/D converter 20 and the access of the memory 30 by the memory control circuit 40 when the data are written into the memory 30. Furthermore, the pulse generator 70 operates to time the access of the memory 30 when the data are read out of the memory 30.

Figure 6:
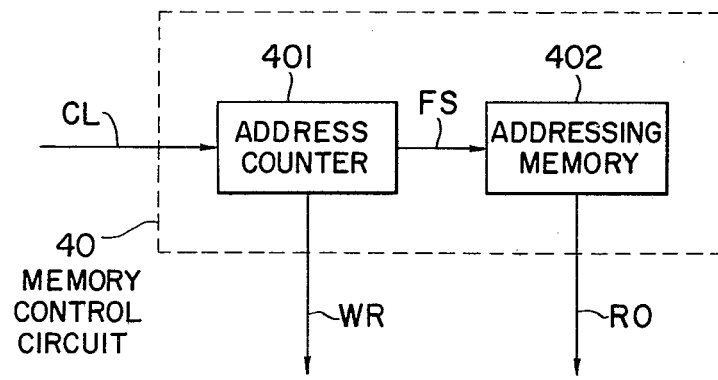
FIG. 6 is a block diagram showing one example of a memory control circuit 40.
Figures 7, 8:
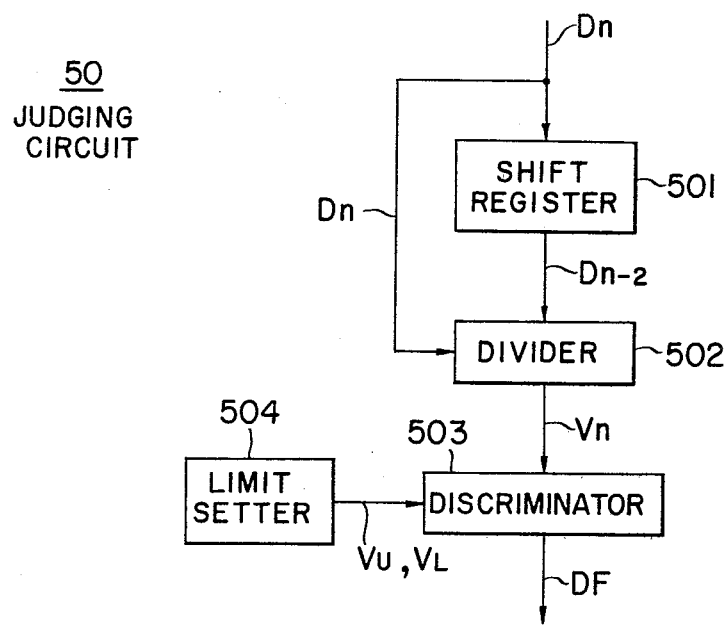
FIG. 7 is a diagram showing data stored in a memory 30.
FIG. 8 is a block diagram showing one example of a judging circuit 50.

The memory control circuit 40 is formed for instance as shown in FIG. 6. The output clock signal CL of the pulse generator 70 drives an address counter 401, and according to addresses specified by write signals WR provided by the address counter 401 the digital signals DS of the A/D converter 20 are successively stored in the memory 30. The video signal of the object provided by the television camera is divided into picture elements which are arranged 100 in the X direction and 100 in the Y direction as shown in FIG. 7. Thus, the picture element signals are stored in the memory 30 at addresses which respectively correspond to the picture elements arranged in a matrix form of 100×100. In this case, addressing is made in a sequence described below. First, with Y=1 fixed, X=1 through X=100 are specified in the stated order. Then, with Y=2 fixed, X=1 through X=100 are specified in the stated order. Similarly, the remaining addresses are specified. After all of the addresses have been specified as described above, reading the data is started. In the data reading operation, the output clock signal CL of the pulse generator 70 is counted by the address counter 401, and the output (memory read-out signal) FS of the address counter 401 is applied to an addressing memory (ROM) 402, and the addressing memory 402 provides the read signal RO to the memory (RAM) 30 for addressing according to Table 1 (a)-(c). Table 1 indicates an example of a code conversion, concerning the central portion of the bottle bottom.

TABLE 1

| C | X | Y | C | X | Y | C | X | Y |
|---|---|---|---|---|---|---|---|---|
| 0 | 50 | 51 | 61 | 53 | 53 | 122 | 46 | 56 |
| 1 | 50 | 50 | 62 | 54 | 52 | 123 | 47 | 57 |
| 2 | 49 | 50 | 63 | 54 | 51 | 124 | 48 | 57 |
| 3 | 49 | 51 | 64 | 54 | 50 | 125 | 49 | 57 |
| 4 | 49 | 52 | 65 | 54 | 49 | 126 | 50 | 57 |
| 5 | 50 | 52 | 66 | 53 | 48 | 127 | 51 | 57 |
| 6 | 51 | 51 | 67 | 53 | 47 | 128 | 52 | 57 |
| 7 | 51 | 50 | 68 | 52 | 47 | 129 | 53 | 56 |
| 8 | 50 | 49 | 69 | 51 | 46 | 130 | 54 | 55 |
| 9 | 49 | 49 | 70 | 50 | 46 | 131 | 55 | 54 |
| 10 | 48 | 50 | 71 | 49 | 46 | 132 | 56 | 53 |
| 11 | 48 | 51 | 72 | 48 | 46 | 133 | 56 | 52 |
| 12 | 48 | 52 | 73 | 47 | 47 | 134 | 56 | 51 |
| 13 | 48 | 53 | 74 | 46 | 47 | 135 | 56 | 50 |
| 14 | 49 | 53 | 75 | 46 | 48 | 136 | 56 | 49 |
| 15 | 50 | 53 | 76 | 45 | 49 | 137 | 56 | 48 |
| 16 | 51 | 53 | 77 | 45 | 50 | 138 | 55 | 47 |
| 17 | 51 | 52 | 78 | 45 | 51 | 139 | 54 | 46 |
| 18 | 52 | 52 | 79 | 45 | 52 | 140 | 53 | 45 |
| 19 | 52 | 51 | 80 | 45 | 53 | 141 | 52 | 44 |
| 20 | 52 | 50 | 81 | 45 | 54 | 142 | 51 | 44 |
| 21 | 52 | 49 | 82 | 46 | 55 | 143 | 50 | 44 |
| 22 | 51 | 49 | 83 | 47 | 55 | 144 | 49 | 44 |
| 23 | 51 | 48 | 84 | 47 | 56 | 145 | 48 | 44 |
| 24 | 50 | 48 | 85 | 48 | 56 | 146 | 47 | 44 |
| 25 | 49 | 48 | 86 | 49 | 56 | 147 | 46 | 45 |
| 26 | 48 | 48 | 87 | 50 | 56 | 148 | 45 | 46 |
| 27 | 48 | 49 | 88 | 51 | 56 | 149 | 44 | 47 |
| 28 | 47 | 49 | 89 | 52 | 56 | 150 | 43 | 48 |
| 29 | 47 | 50 | 90 | 52 | 55 | 151 | 43 | 49 |
| 30 | 47 | 51 | 91 | 53 | 55 | 152 | 43 | 50 |
| 31 | 47 | 52 | 92 | 54 | 54 | 153 | 43 | 51 |
| 32 | 47 | 53 | 93 | 54 | 53 | 154 | 43 | 52 |
| 33 | 48 | 54 | 94 | 55 | 53 | 155 | 43 | 53 |
| 34 | 49 | 54 | 95 | 55 | 52 | 156 | 43 | 54 |
| 35 | 50 | 54 | 96 | 55 | 51 | 157 | 43 | 55 |
| 36 | 51 | 54 | 97 | 55 | 50 | 158 | 44 | 55 |
| 37 | 52 | 53 | 98 | 55 | 49 | 159 | 44 | 56 |
| 38 | 53 | 52 | 99 | 55 | 48 | 160 | 45 | 56 |
| 39 | 53 | 51 | 100 | 54 | 48 | 161 | 45 | 57 |
| 40 | 53 | 50 | 101 | 54 | 47 | 162 | 46 | 57 |
| 41 | 53 | 49 | 102 | 53 | 46 | 163 | 47 | 58 |
| 42 | 52 | 48 | 103 | 52 | 46 | 164 | 48 | 58 |
| 43 | 51 | 47 | 104 | 52 | 45 | 165 | 49 | 58 |
| 44 | 50 | 47 | 105 | 51 | 45 | 166 | 50 | 58 |
| 45 | 49 | 47 | 106 | 50 | 45 | 167 | 51 | 58 |
| 46 | 48 | 47 | 107 | 49 | 45 | 168 | 52 | 58 |
| 47 | 47 | 48 | 108 | 48 | 45 | 169 | 53 | 57 |
| 48 | 46 | 49 | 109 | 47 | 45 | 170 | 54 | 57 |
| 49 | 46 | 50 | 110 | 47 | 46 | 171 | 54 | 56 |
| 50 | 46 | 51 | 111 | 46 | 46 | 172 | 55 | 56 |
| 51 | 46 | 52 | 112 | 45 | 47 | 173 | 55 | 55 |
| 52 | 46 | 53 | 113 | 45 | 48 | 174 | 56 | 55 |
| 53 | 46 | 54 | 114 | 44 | 48 | 175 | 56 | 54 |
| 54 | 47 | 54 | 115 | 44 | 49 | 176 | 57 | 53 |
| 55 | 48 | 55 | 116 | 44 | 50 | 177 | 57 | 52 |
| 56 | 49 | 55 | 117 | 44 | 51 | 178 | 57 | 51 |
| 57 | 50 | 55 | 118 | 44 | 52 | 179 | 57 | 50 |
| 58 | 51 | 55 | 119 | 44 | 53 | | | |
| 59 | 52 | 54 | 120 | 44 | 54 | | | |
| 60 | 53 | 54 | 121 | 45 | 55 | | | |

In the device thus organized, the bottle 10 to be examined which is conveyed by a conveying means such as a conveyor is irradiated through the diffusing plate 12 by the lamp, and when the bottle reaches a predetermined position, the optical image of the bottle bottom is picked up by the television camera 13, so that one frame of the optical image is subjected to photoelectric conversion and is delivered as the video signal VS. The analog video signal VS is converted into the digital signal DS according to its brightness by the A/D converter 20, and is stored in the address of the memory 30, which is specified by the write signal WR from the addressing circuit 401, as shown in FIG. 7. The data stored in the memory 30 are read out in the order in which the addresses are specified by the read signals RO outputted by the addressing memory 402 which is driven by the pulse generator 70. In this case, the addressing is carried out successively in correspondence to the spiral scanning positions beginning with the center CP of the bottle bottom as shown in FIG. 4A, according to Table 1. Therefore, if the bottle bottom has no defect, the memory 30 outputs a signal whose level is gradually changed as shown in FIG. 4B. On the other hand, if the bottle bottom has a defect, the data read out of the memory 30 is changed abruptly in level. This abrupt change is detected by the judging circuit 50.

The judging device 50 may for example be formed as shown in FIG. 8. During a reading cycle, data $D_n$ is read out of the memory 30 and is fed to a shift register 501, which, when another data is read out of the memory 30, i.e., during a later reading cycle lagging behind the first mentioned reading cycle by two reading cycles, outputs the previously stored data. A divider 502 divides the data $D_n$ read out of the memory 30 by the data $D_{n-2}$ outputted by the register 501 and produces a signal indicative of the ratio $V_n (=D_n/D_{n-2})$ of the data $D_n$ to the data $D_{n-2}$ read out at the earlier reading cycle. A discriminator 503 judges whether the ratio $V_n$ is within a range defined by an upper limit $V_U(>1)$, e.g., 1.5 and a lower limit $V_L(<1)$, e.g., 1/1.5 set by a limit setter 504. If, as a result of the judgement, the ratio $V_n$ is found to be outside the range, a defect signal DF is produced. This signal DF indicates that the bottle being examined has a defect because of which the bottle should be rejected. The signal DF is supplied to a reject device 60, which removes the bottle from the conveyor line.

Figure 9:
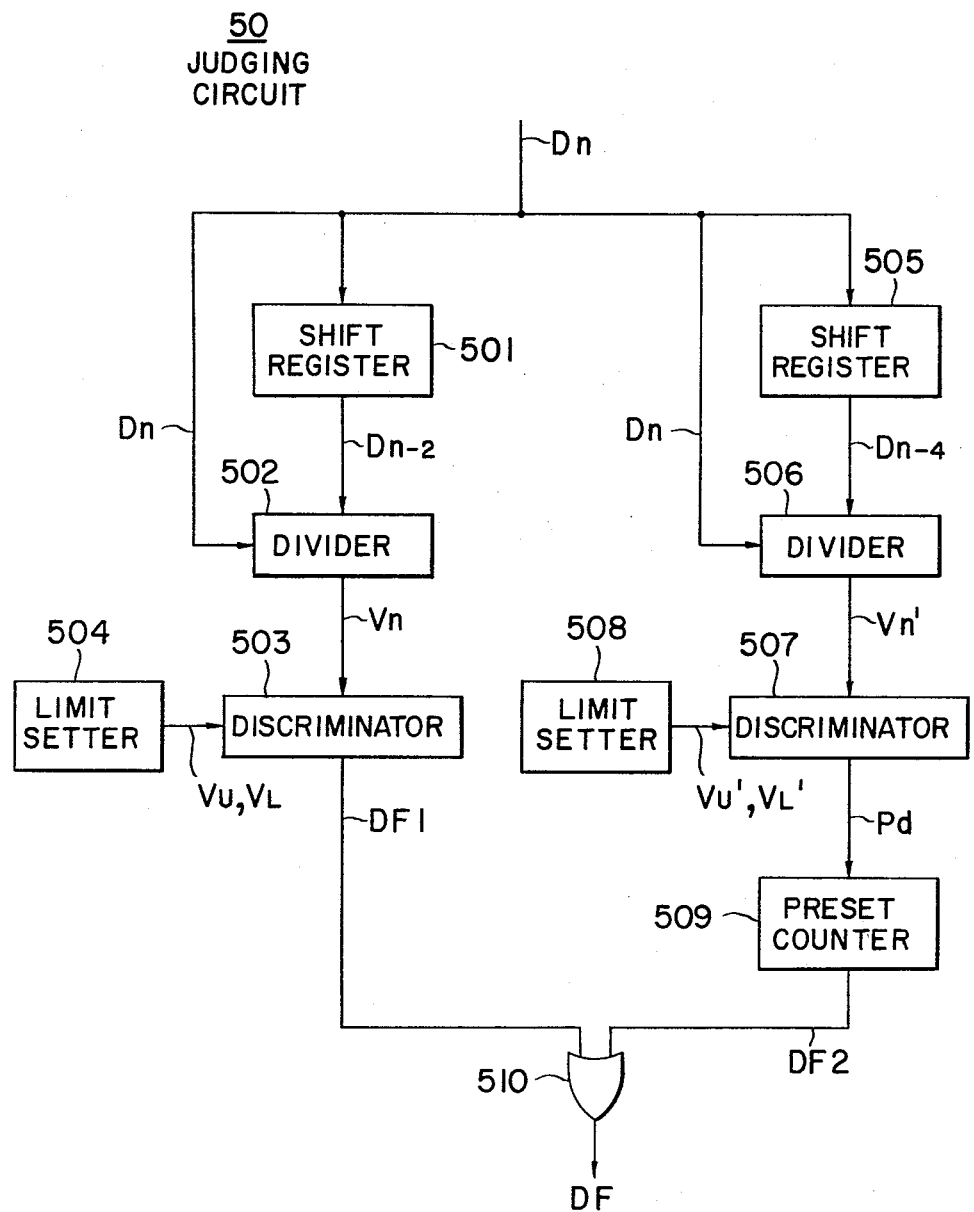
FIG. 9 is a block diagram showing another example of a judging circuit 50.

Another example of judging device 50 is shown in FIG. 9. As shown, it comprises a shift register 501, a divider 502, a discriminator 503 and a limit setter 504 which are respectively similar to those identified by the same reference numerals. The output of the discriminator 503 is indicated by DF1, rather than DF, for the reason which will be apparent from the following description. The judging device 50 of FIG. 9 additionally comprises a second shift register 505. The shift register 505 stores and shifts the data read out of the memory 30. After four reading cycles, data $D_{n-4}$ is outputted. A second divider 506 divides the data $D_n$ read out of the memory 30 at the current reading cycle by the data $D_{n-4}$ outputted by the shift register 505 and produces the ratio $V_n' (=D_n/D_{n-4})$. A second discriminator 507 judges whether the ratio $V_n'$ is within a range defined by an upper limit $V_U'(>1)$, e.g., 1.1 and a lower limit $V_{L'}(<1)$, e.g., 1/1.1 set by a second limit setter 508. The upper limit $V_U'$ and the lower limit $V_L'$ are respectively closer to 1 (unity) than $V_U$ and $V_L$. When the ratio $V_n'$ is found to be outside the range, an output pulse Pd is produced. A preset counter 509 counts the number of pulses from the discriminator 507 and upon counting the preset number (e.g., six) of pulses from the discriminator 509, the counter 509 produces an output signal DF2. Either of the signals DF1 and DF2 passes through an OR gate 510 to serve as a defect signal.

With the provision of the shift register 505, the divider 506, the discriminator 507, the limit setter 508 and the preset counter 509, it is possible to detect a defect which varies the brightness only slightly but over an extensive area or length.

Figure 10A:
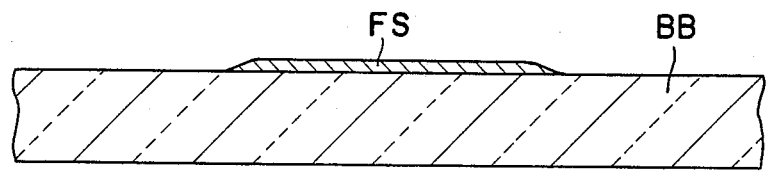
FIGS. 10A, 10B and 10C are diagrams showing how a faint stain is detected.
Figure 10B:
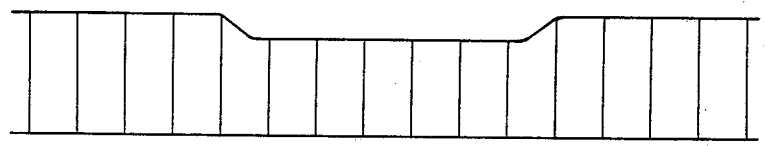
Figure 10C:

For instance, if a faint stain FS attached extensively over a bottom BB of a bottle as shown in FIG. 10A, the brightness data $D_n$ sequentially read out of the memory 30 will have values respectively as shown in FIG. 10B. As will be appreciated, none of the pairs of a data value and another data value read out in advance by two reading cycles result in a ratio outside the range ($V_L < V_n < V_U$), so that the discriminator 503 will not produce a signal DF1. But some of the pairs of data spaced each other by three other data result in a ratio outside the range ($V_L' < V_n < V_U'$), so that the discriminator 507 will produce output pulses at timings as shown in FIG. 10C. The output pulses are counted by the counter 509. If the reading of the data of the picture elements corresponding to the stained portion out of the memory 30 occurs successively more than four times, four pulses appear at the beginning as well as after the ends of stained portion. As a result, upon counting of the predetermined number of six, the counter 509 produces a signal DF2, which passes through the OR gate 510. Thus, a defect signal DF indicative of the presence of a defect warranting rejection of the bottle is produced. On the other hand, where the number of pulses from the discriminator 507 is less than the preset number of six because, for instance, the brightness variation is due to presence of a tiny stone in the glass structure of the bottom of the bottle, the bottle will not be rejected.

The number of reading cycles which elapse after the shift register 501 or 505 receives data and before it outputs the same data can be predetermined by selection of the number of register stages or by selection of the output terminals.

It should also be noted that a plurality of combinations each consisting of members similar to the devices 505 through 509 in FIG. 9, with different limit values and counter preset values (and, attendantly, with or without different shift register stages) may be employed and their output may be coupled by an OR gate similar to that 510 shown in FIG. 9. It is generally useful to so determine the limit values and the respectively associated counter preset values that the greater one of the upper limit values is associated with the smaller one of the counter preset values. With such arrangement, variety of stains or presence of foreign matters or cracks which justifies the rejection of the bottle and which causes different degree of brightness variation over different areas can be all detected.

Instead of providing a plurality of combinations of a shift register (501, 505) and a divider (502, 506), only one such combination may be used, with its output being used as input to all of the discriminators (503, 507).

Instead of judging whether or not the ratio between two signals are lower than an upper limit and higher than a lower limit, only one of the limit values may be used. The term "predetermined value range" should therefore be construed as encompassing a range having both of upper and lower limits as well as a range having only one of upper and lower limits.

Instead of resorting to the ratio between two signals for making judgement on the variation of one signal relative to another, difference between two signals may be used.

The value range and the number of reading operations upon which the judgement on the defect is based can be made different for one part (e.g., central part of the bottom of the bottle) and for another part (e.g., peripheral part of the bottom of the bottle).

In the above-described embodiment, the bottle 10 is scanned spirally from the center CP towards the outer edge of the bottom; however, it may be scanned spirally from the outer edge towards the center CP.

Figure 11A:
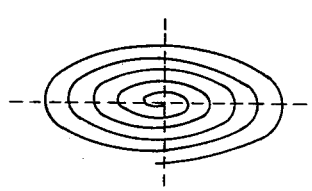
FIGS. 11A, 11B, 11C and 11D are diagrams showing different scanning lines, respectively.
Figure 11B:
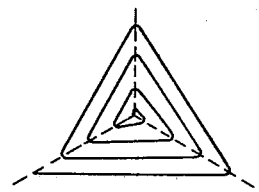
Figure 11C:
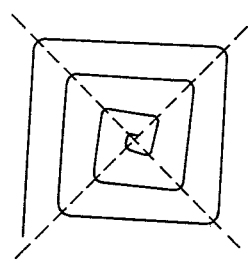
Figure 11D:
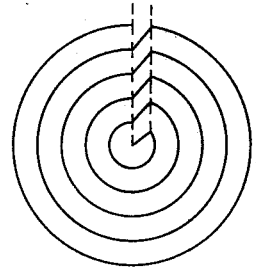

The invention is not limited to the method in which the bottle is scanned along a curve which changes, at a constant rate, in the distance from the center. That is, the configuration of the curve should be defined according to the configuration of the bottle or any other object to be examined. Therefore, the scanning may be carried out along curves as shown in FIGS. 11A, 11B or 11C separately according to the object configurations. Furthermore, a curve as shown in FIG. 11D may be used for a circular portion of the object to be examined. The curve of FIG. 11D is easier to draw than that of FIG. 4A, so that use of the curve of FIG. 11 makes it easier to decide the order of reading the data out of the memory 30. Thus, the term "a substantially spiral line" should be interpreted to include the above-described cases.

The sequence of reading the data out of the memory 30 may be such that the data is read out each time the corresponding bottle segment is traversed by the spiral line. Alternatively, the arrangement may be such that the data which has been read out once is not read out again.

It sometimes occurs that the center of the bottom of the bottle 10 is not accurately aligned with the center of the television camera 13, so that the television camera 13 does not "see" the image of the object 10 at its center. This may be the case if the mechanism for guiding the bottle into position is inaccurately formed or is worn after repeated use, or if the inner annular edge of the bottom of the bottle is eccentric with the outer annular edge (cylindrical surface) of the bottle. In this case, the addresses specified by the memory control circuit 40 scan spirally beginning with the center of the image, and as a result, the signal read out of the memory 30 is not of the curve gradually changed in level, and the signal representative of the corner of the bottle may be mistaken for the defect signal.

Figure 12:
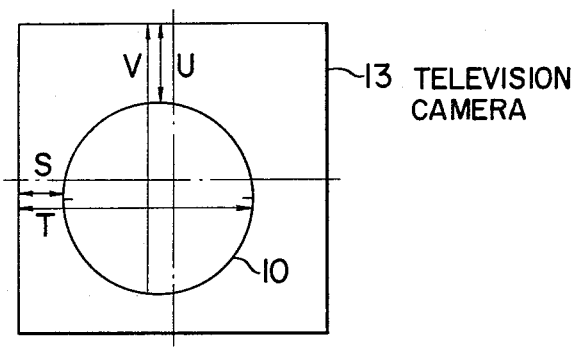
FIG. 12 is a diagram for a description of the correction of addressing data in the invention.
Figure 13:
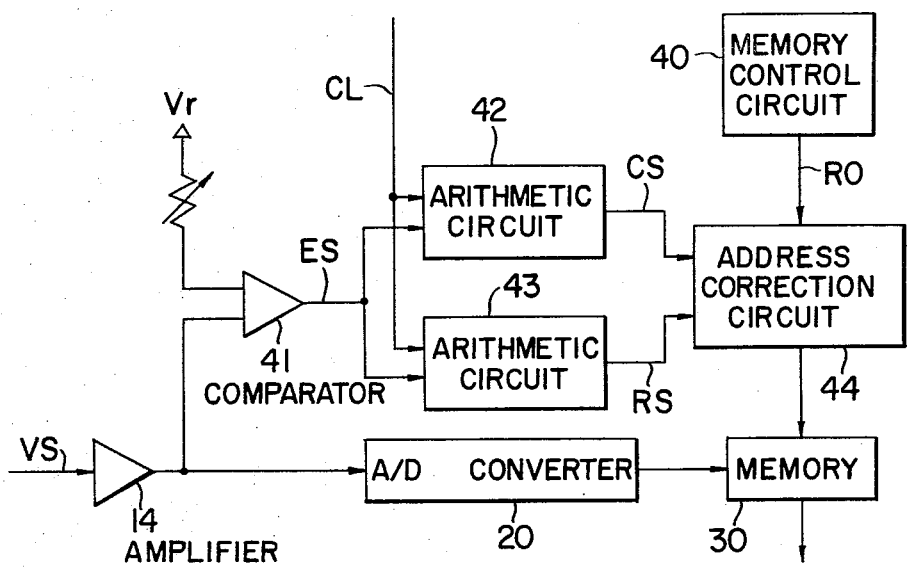
FIG. 13 is a block diagram showing one example of circuit for correcting addressing data.

In order to eliminate this difficulty, the following method can be employed: In the positional relationship between the bottle 10 and the television camera 13 as shown in FIG. 12, calculations (S+T)/2 and (U+V)/2 are carried out respectively for horizontal and vertical shifts, and the center thereof is obtained to correct the difference from the reference. One circuit for implementing this method is as shown in FIG. 13. A comparator 41 is provided to compare a reference voltage Vr with the output of an amplifier 14 thereby to obtain an edge signal ES indicating the inner edge of the bottom of the bottle. From the edge signal thus obtained, a center signal CS in the vertical direction is obtained by an arithmetic circuit 42 and a center signal RS in the horizontal direction is obtained by an arithmetic circuit 43. These center signals CS and RS are applied to address correcting circuit 44, and the contents, or addresses, of the read signals RO provided by the memory control circuit 40 are corrected and the spiral scanning is carried out beginning with the center of the bottle.

As is apparent from the above description, with the defect detecting device according to the invention, the memory data are read out by addressing them through the utilization of the spiral scanning in order to eliminate the optical disturbance which is caused in the corner of a bottle to be examined, and therefore the defects can be detected with high accuracy at high speed, and yet the device can be manufactured at low cost.

In the above-described embodiment, light is applied from under the bottle and is received over the bottle; however, it will be appreciated that the light may be applied from over the bottle and received under the bottle. The invention is not limited to detection of defect in a bottle, but is applicable to detection of defect in any other object. The television camera for receiving light passed through the object may be an image orthicon camera or a vidicon camera or one using a solid image pickup element such as a CCD (charge coupled device), or BBD (bucket brigade device).

Furthermore, in the above-described embodiment, the analog video signal, after being converted into the digital signal by the A/D converter, is stored in the digital memory; however, it is possible to store the analog video signal in an analog memory.

What is claimed is:

1. A defect detecting method comprising the steps of:
   illuminating an object to be examined;
   receiving light from said object to form in image forming means the impage of said object;
   dividing the image of said object into a plurality of picture elements;
   storing in signal storing means the signals of said picture elements in relation with the positions of portions of said objects to which said picture elements correspond respectively;
   reading the signals of said picture elements in order in which the portions of said object corresponding respectively to said picture elements are traversed by a substantially spiral imaginary line which is drawn on said object; and
   detecting a defect in said object from the mutual relationship between the signal of one of the picture elements and the signal of another picture element read out a little before the reading of the signal of said one of the picture elements and the variation of the signal of one of the picture elements relative to the signal of another picture element is found to be outside a predetermined value range.

2. A method as claimed in claim 1, in which the step of detecting a defect comprises judging that said object has a defect if finding that the variation of the signal of one of the picture elements relative to the signal of another picture element read out in advance by a predetermined number of reading operations is outside a predetermined value range is repeated a predetermined number of times.

3. A method as claimed in claim 1, in which the step of detecting a defect comprises judging that the object has a defect if at least one of predetermined conditions is satisfied, wherein each of said conditions is that finding that the variation of the signal of one of the picture elements relative to the signal of another picture element read out in advance by a predetermined number of reading operations is outside a predetermined value range is repeated a predetermined number of times, and each of the value ranges and the associated number of times are so determined that a greater one of the value ranges is associated with a smaller one of the numbers of times.

4. A method as claimed in claims 1, 2 or 3, in which said variation of the signal of one of the picture elements relative to the signal of another picture element consists of the ratio of the signal of one of the picture elements to the signal of another picture element.

5. A defect detecting device comprising:
   means for illuminating an object to be examined;
   means for receiving light from said object, to form the image of said object;
   storing means for storing signals representative of picture elements forming said image in relation to portions of said object which correspond to said picture elements, respectively;
   reading means for reading said signals representative of said picture elements in the order in which the portions of said object to which said picture elements correspond respectively are traversed by a substantially spiral imaginary line which is drawn on said object; and
   detecting means for detecting a defect in said object from the mutual relationship between the signal of one of the picture elements and the signal of another picture element read out a little before the reading of the signal of said one of the picture elements, said detecting means having means for judging that said object has a defect if the variation of the signal of one of the picture elements relative to the signal of another picture element is found to be outside a predetermined value range.

6. A device as claimed in claim 5, in which said detecting means comprises means for judging that said object has a defect if finding that the variation of the signal of one of the picture elements relative to the signal of another picture element read out in advance by a predetermined number of reading operations is outside a predetermined value range is repeated a predetermined number of times.

7. A device as claimed in claim 6, in which said detecting means comprises means for judging that the object has a defect if at least one of the predetermined conditions is satisfied, wherein each of said conditions is that finding that the variation of the signal of one of the picture elements relative to the signal of another picture element read out in advance by a predetermined number of reading operations is outside a predetermined value range is repeated a predetermined number of times, and each of the value ranges and the associated number of times are so determined that a greater one of the value ranges is associated with a smaller one of the numbers of times.

8. A device as claimed in claims 5, 6 or 7 in which said variation of the signal of one of the picture elements relative to the signal of another picture element consists of the ratio of the signal of one of the picture elements to the signal of another picture element.

9. A device as claimed in claim 5, further comprises:
   means for detecting the edge of said objects; and
   means for correcting, according to the result of detection of the edge of said object, addresses which are specified by said means.

* * * * *